(12) United States Patent
Katayama et al.

(10) Patent No.: US 8,558,033 B2
(45) Date of Patent: Oct. 15, 2013

(54) PROCESS FOR PRODUCING OPTICALLY ACTIVE ALIPHATIC FLUOROALCOHOL

(75) Inventors: Takeaki Katayama, Saitama (JP); Toshihide Takemoto, Saitama (JP); Kunihiko Murata, Saitama (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 6 days.

(21) Appl. No.: 13/170,347

(22) Filed: Jun. 28, 2011

(65) Prior Publication Data

US 2011/0319671 A1 Dec. 29, 2011

(30) Foreign Application Priority Data

Jun. 28, 2010 (JP) ................. 2010-146219

(51) Int. Cl.
*C07C 29/143* (2006.01)
(52) U.S. Cl.
USPC ....................................................... 568/842
(58) Field of Classification Search
USPC ....................................................... 568/842
See application file for complete search history.

(56) References Cited

U.S. PATENT DOCUMENTS

2008/0221327 A1   9/2008 Pfleger et al.

FOREIGN PATENT DOCUMENTS

| JP | 09-157196 | 6/1997 |
|---|---|---|
| JP | 09-301929 A | 11/1997 |
| JP | 2962668 B2 | 8/1999 |
| JP | 4090078 B2 | 3/2008 |
| JP | 2009-544653 A | 12/2009 |
| WO | WO 98/42643 A1 | 10/1998 |
| WO | WO 2008/012240 A1 | 1/2008 |
| WO | WO 2008/107334 A2 | 9/2008 |

OTHER PUBLICATIONS

Ramachandran, P. V. et al., "Chiral Synthesis via Organoboranes. 40. Selective Reductions. 55. Simple One-Pot Synthesis of the Enantiomers of (Trifluoromethyl)oxirane. A General Synthesis in High Optical Purities of α-Trifluoromethyl Secondary Alcohols via the Ring-Cleavage Reactions of the Epoxide," *J. Org. Chem.* 1995; 60:41-46.
Schaus, S.E. et al., "Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Diols," *J. Am. Chem. Soc.* 2002; 124(7):1307-1315.
Šterk, D. et al., "Highly Enantioselective Transfer Hydrogenation of Fluoralkyl Ketones," *Organic Letters* 2006; 8(26):5935-5938.
Thiel, O.R. et al., "Development of a Practical Synthesis of a p38 MAP Kinase Inhibitor," *Organic Process Research and Development* 2009; 13(2):230-241.
Wu, X. et al., "Accelerated asymmetric transfer hydrogenation of aromatic ketones in water," *Org. Biomol. Chem.* 2004; 2:1818-1821.
Wu, X. et al., "Insight into and Practical Application of pH-Controlled Asymmetric Transfer Hydrogenation of Aromatic Ketones in Water," *Angew. Chem. Int. Ed.* 2005; 44:3407-3411.

*Primary Examiner* — Sikarl Witherspoon
(74) *Attorney, Agent, or Firm* — Wolf, Greenfield & Sacks, P.C.

(57) ABSTRACT

The problem to be resolved by the present invention is to provide a method for efficiently synthesizing optically active lower aliphatic alcohols that have difficulty in separation from organic solvents, without using a special reactor.
The present invention relates to a method for producing an optically active aliphatic alcohol having a fluorine atom at α position, wherein an optically active alcohol is produced by reacting an aliphatic ketone having a fluorine atom at α position in water using a formate, under the presence of an asymmetric catalyst represented by general formula (1) and an acid.

11 Claims, No Drawings

PROCESS FOR PRODUCING OPTICALLY ACTIVE ALIPHATIC FLUOROALCOHOL

TECHNICAL FIELD

The present invention relates to a process for producing optically active aliphatic fluoroalcohols. More specifically, the invention in this application relates to a process for producing optically-active and physiologically-active compounds employed for pharmaceuticals and agrochemicals, or optically active aliphatic fluoroalcohols useful as synthetic intermediates of liquid crystal materials, etc.

BACKGROUND ART

There are many naturally-occurring organic compounds which are in a form of optically active substances. Among the compounds having physiological activities, a desirable activity is frequently present in only one type of their optical isomers. Furthermore, it is also known that the other optical isomer without the desirable activity does not have a useful physiological activity for living organisms, rather, sometimes it has a toxicity for living organisms. Accordingly, as a safe method for the synthesis of pharmaceuticals, development of a method for synthesizing objective compounds, or optically active compounds having a high optical purity as intermediates of the objective compounds, has been desired.

Optically active alcohols are useful as asymmetric sources for synthesizing various optically active substances. In general, optically active alcohols are produced by optical resolution of racemic bodies, or by asymmetric synthesis using a biological catalyst or an asymmetric metal complex as a catalyst. In particular, production of optically active alcohols by asymmetric synthesis is considered to be indispensable for producing a large amount of optically active alcohols.

Optically active fluoroalcohols are one of the optically active alcohols that are industrially useful as synthetic intermediates of optically-active and physiologically-active compounds employed for pharmaceuticals and agrochemicals, or as synthetic intermediates of liquid crystal materials. For example, optically active 1,1,1-trifluoro-2-propanol is a synthetic intermediate of glycine transport inhibitors, and is effective for the treatment of mental diseases such as Alzheimer's dementia, mania, and depression (Patent Literature 1), and is also employed as synthetic intermediates of p38 MAP kinase inhibitors (Non Patent Literature 1). In addition, optically active 1,1,1-trifluoro-2-butanol is used as a synthetic intermediate of antiferroelectric liquid crystal compounds, realizing high-speed responsiveness (Patent Literature 2).

Synthetic methods of optically active fluoroalcohols are roughly classified into methods employing microorganisms and chemical methods. As methods employing microorganisms, there are reports on a method to use selective hydrolysis of esters, a method for asymmetric reduction of fluoroketones and so on. Examples of chemical methods include optical resolution, asymmetric hydrogenation, and asymmetric reduction. These methods are exemplified below.

As an example of employing selective hydrolysis of esters by microorganisms, there is a report on a method to synthesize optically active 1,1,1-trifluoro-2-butanol by enantioselective alcoholysis of corresponding ester with lipase (Patent Literature 2). With this method, the objective substance is obtained by extraction of a product using methylene chloride; however, a half of the raw material used becomes unnecessary, which is inefficient. In addition, there exists a problem of difficulty in complete distillation of a solvent away, as well as a problem of low yield.

As an example of reduction using microorganisms, a method for obtaining 1,1,1-trifluoro-2-propanol by reaction of 1,1,1-trifluoro acetone with a baker's yeast in a buffer solution has been known (Patent Literature 1), in which for the recovery of the objective substance from the buffer solution, extraction with an organic solvent or direct distillation is used. However, in the case of extraction with an organic solvent, separation from the organic solvent used is difficult due to the fairly low boiling point of 82° C. of alcohol. In the case of distillation from a buffer solution, since alcohol with a low concentration in the buffer solution are to be distilled, it is difficult to obtain the objective alcohol with a high yield.

As an example of kinetic resolutions, the following method has been known: racemic (trifluoromethyl)ethylene oxide is enantioselectively hydrated under the presence of a cobalt-salen complex catalyst, then (trifluoromethyl)ethylene oxide which remains without being reacted is separated to obtain optically active (trifluoromethyl ethylene oxide); then, by reacting this with hydrogenated lithium aluminum, optically active 1,1,1-trifluoro-2-propanol is obtained. However, this can hardly be an efficient synthetic method by separation, because a half of the raw material used becomes unnecessary (Non Patent Literature 2).

As an example of using asymmetric hydrogenation catalysts, a method wherein 1,1,1-trifluoroacetone is subjected to hydrogenated pressurization under the presence of an asymmetric hydrogenation catalyst has been known (Patent Literature 3). However, high-pressure hydrogen of 40 MPa or more must be used, requiring a corresponding high-pressure reactor; thus, it is not an easy method.

As an example of asymmetric reduction using an organic substance as a hydrogen source, the following method has been known: 1,1,1-trifluoroacetone having a halogen atom at position 3 is reduced by an optically-active borane reducing agent to synthesize optically active 3-halo-1,1,1-trifluoro-2-propanol, and this substance is converted into optically active (trifluoromethyl)ethylene oxide by the reaction with sodium hydroxide, then this is treated with lithium aluminum hydride to obtain optically active 1,1,1-trifluoro-2-propanol. In this method however, an expensive optically-active substance is used at a stoichiometric amount, and the reaction is a multi-step reaction; thus, this is hardly said to be an efficient method (Non Patent Literature 3).

Focusing on asymmetric reduction catalysts which enable synthesis of optically active alcohols from corresponding ketones via one-step reaction with which no special reactor is required, asymmetric ruthenium, rhodium and indium catalysts having sulfonyl diamine as a ligand have been known to be useful asymmetric reduction catalysts (Patent Literature 4, Patent Literature 5). As an example of synthesis of fluoroalcohols using such method, a case wherein 1,1,1-trifluoroketone is asymmetrically reduced in formic acid/triethylamine under the presence of an asymmetric ruthenium catalyst has been known (Non Patent Literature 4). However, with this method, a post-treatment to remove formic acid and triethylamine by washing with water is necessary after the reaction solution is dissolved in a solvent. Because of this process, in cases of alcohols having a boiling point close to that of a solvent, separation from the solvent becomes difficult in some cases. In fact, in this literature, only a case of 1,1,1-trifluoro-2-octanone having a fairly high boiling point with which solvent extraction and washing with water are possible is described as an example of the reaction of aliphatic ketones, and synthesis of fluoroalcohols having a low boiling point which easily dissolve in water, such as 1,1,1-trifluoro-2-propanol, is not at all mentioned.

Meanwhile, in hydrogen-transfer type asymmetric reduction of ketones using ruthenium, iridium or rhodium catalyst having the above sulfonyl diamine as a ligand, the following 2-phase reduction has been known (Non Patent Literature 5, Non Patent Literature 6); namely, in water as a solvent, reaction is carried out in a state of separation of 2 phases of water-organic layers, using formate as a hydrogen source; and it has been reported that pH affects the catalyst reaction. For example, when reduction is carried out using formic acid/triethylamine as a hydrogen source, and when the amounts of formic acid and triethylamine are changed to change the pH value of the reaction solution, then the reaction rate and optical purity of the alcohol obtained are known to be affected (Non Patent Literature 6). However, in this literature, only a synthetic method of optically active aromatic alcohols using aromatic ketones as a substrate has been described, and synthesis of optically active aliphatic fluoroalcohols such as 1,1,1-trifluoro-2-propanol using an aliphatic ketone having a fluorine atom at α position as a substrate has not been mentioned.

CITATION LIST

Patent Literature

Patent Literature 1: WO2008/107334
Patent Literature 2: JP, A, 9-301929
Patent Literature 3: JP, A, 2009-544653
Patent Literature 4: Japanese Patent No. 2962668
Patent Literature 5: Japanese Patent No. 4090078

Non Patent Literature

Non Patent Literature 1: O. R. Thiel, M. Achmatowicz, C. Bernard et al., Organic Process Research & Development, 2009, 13(2), 230-241.
Non Patent Literature 2: S. E. Schhaus, B. D. Brandes, E. N. Jacobsen et al., Journal of the American Chemical Society, 2002, 124, 1307-1315.
Non Patent Literature 3: P. V. Ramachandran, B. Gong, H. C. Brown, Journal of Organic Chemistry, 1995, 60, 41-46.
Non Patent Literature 4: D. Sterk, M. Stephan, B. Mohar, Organic Letters, 2006, 26(8), 5953-5938.
Non Patent Literature 5: X. Wu, X. Li, W. Hems, F. Hems, F. King, J. Xiao, Org. Biomol. Chem. 2004, 2, 1818.
Non Patent Literature 6: X. Wu., X. Li, F. King, J. Xiao, Angew. Chem. Int. Ed., 2005, 44, 3407-3411.

SUMMARY OF THE INVENTION

Problems to be Resolved by the Invention

A problem to be resolved by the present invention is to provide an efficient synthetic method of optically active aliphatic fluoroalcohols, in particular optically active lower aliphatic fluoroalcohols having a carbon number of 3 to 5 with which separation from solvent is difficult, without using a special reactor. However, present inventors have, in their intensive investigation, faced a new problem that alcohol cannot be collected although ketone substrates do not remain.

Means of Solving the Problems

The present inventors have found that, as an efficient synthetic method without using a special reactor, the reaction proceeds rapidly by using 2-phase reduction condition with water as a solvent, under the presence of a metal complex. In this method, because water is used as the solvent, optically active fluoroalcohols with a high purity can be obtained by a simple operation of distillation of the reaction solution.

As a countermeasure for the disadvantageous phenomenon wherein yield of alcohol obtained decreases although a ketone used as a raw material does not remain, the present inventors have also found that, in their successive investigation, yields can be significantly increased by addition of an acid; thus, the present invention has been accomplished.

Therefore, the present invention relates to a process for producing an optically active fluoroalcohol, in which, under the presence of an acid and an asymmetric catalyst that is a metal complex represented by general formula (1):

[Chem. 1]

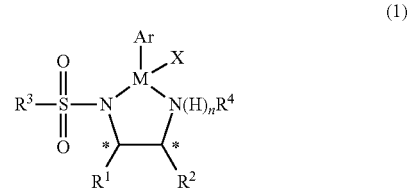

wherein $R^1$ and $R^2$ may be identical to or different from each other, and are one selected from the group consisting of a hydrogen atom, an alkyl group that may have a substituent, a phenyl group that may have a substituent, a naphthyl group that may have a substituent, a cycloalkyl group that may have a substituent, and an unsubstituted or substituted alicyclic ring formed by binding $R^1$ and $R^2$,
$R^3$ is one selected from the group consisting of an alkyl group that may have a substituent, a perfluoroalkyl group, a phenyl group that may have a substituent, a naphthyl group that may have a substituent, a cycloalkyl group that may have a substituent, a benzyl group that may have a substituent, a piperidinyl group that may have a substituent, a pyrrolidinyl group that may have a substituent, and a camphor group that may have a substituent,
$R^4$ is a hydrogen atom or an alkyl group,
Ar is benzene that may have a substituent or a cyclopentadienyl group that may have a substituent, which binds to M via a π bond,
X is an anionic group,
M is ruthenium, rhodium or iridium,
n denotes either 0 or 1, and when n is 0, then X is absent, and
* denotes an asymmetric carbon;
an aliphatic ketone having one or more fluorine atoms at α position is reacted to produce an optically active alcohol in a solvent containing water, using a formate as a hydrogen source.

In addition, the present invention relates to the production process according to claim 1, wherein the solvent containing water consists of only water.

Furthermore, the present invention relates to said production process, wherein the formate is potassium formate and/or sodium formate.

In addition, the present invention relates to said production process, wherein the acid is formic acid and/or acetic acid.

Furthermore, the present invention relates to said production process, wherein the amount of addition of the acid is in the range from 0.01 to 1 molar equivalent relative to the ketone.

In addition, the present invention relates to said production process, characterized in that the reaction is carried out in the presence of phase-transfer catalyst.

In addition, the present invention relates to said production process, characterized in that the aliphatic ketone having one or more fluorine atoms at α position is a compound represented by general formula (2):

[Chem. 2]

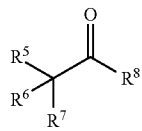

(2)

wherein $R^5$, $R^6$ and $R^7$ are hydrogen, fluorine, or an alkyl group with a carbon number of 1 to 5 which may contain a heteroatom (except that at least one of $R^5$, $R^6$ and $R^7$ is a fluorine atom), $R^8$ is an alkyl group with a carbon number of 1 to 6 which may contain a heteroatom.

Furthermore, the present invention relates to said production process, wherein $R^5$, $R^6$ and $R^7$ are hydrogen, fluorine, or an alkyl group with a carbon number of 1 to 2 which may contain a heteroatom (except that at least one of $R^5$, $R^6$ and $R^7$ is a fluorine atom), $R^8$ is an alkyl group with a carbon number of 1 to 3 which may contain a heteroatom excluding a fluorine atom.

In addition, the present invention relates to said production process, wherein $R^5$, $R^6$ and $R^7$ are hydrogen or fluorine (except that at least one of them is a fluorine atom), $R^8$ is an alkyl group with a carbon number of 1 to 2.

Furthermore, the present invention relates to said production process, wherein the aliphatic ketone having one or more fluorine atoms at α position is 1,1,1-trifluoroacetone.

In addition, the present invention relates to said production process, characterized in that after completion of the reaction, an optically active fluoroalcohol is obtained by distillation of the objective substance from the reaction solution without extraction with a solvent.

Advantageous Effects of the Invention

The present invention enables, with the above constitution, efficient synthesis of optically active lower aliphatic fluoroalcohols of which separation from solvent is difficult, without using a special reactor. Furthermore, the present invention can resolve disadvantageous phenomenon of low yield of alcohol despite that no substrate remains after completion of the reaction, by means of acid addition. The above effects cannot be explained by prior findings that the value of pH affects reaction rate and optical purity in known reaction systems, because ketone as a raw material does not remain (there is no difference in conversion) regardless of presence/absence of addition of acid. The reaction mechanism of this acid is inapparent, but the addition of acid is considered to have effects of suppressing degradation and denaturation of ketones having a fluorine atom at α position or of alcohol generated.

EMBODIMENTS FOR CARRYING OUT THE INVENTION

The asymmetric catalyst of the present invention is a metal complex represented by general formula (1):

[Chem. 3]

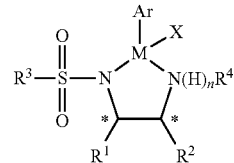

(1)

wherein * denotes an asymmetric carbon.

In general formula (1), $R^1$ and $R^2$ may be identical to or different from each other, and are one selected from the group consisting of hydrogen atom, alkyl group that may have a substituent, phenyl group that may have a substituent, naphthyl group that may have a substituent, cycloalkyl group that may have a substituent, and unsubstituted or substituted alicyclic ring formed by binding $R^1$ and $R^2$.

Examples of the alkyl group that may have a substituent include, but are not limited to, linear or branched alkyl group with a carbon number of 1 to 10 such as methyl group, ethyl group, n-propyl group, isopropyl group, n-butyl group, sec-butyl group, tert-butyl group, etc., and the above linear or branched alkyl group having a halogen atom such as fluorine, chlorine, bromine and iodine, etc. Examples of the phenyl group that may have a substituent include, but are not limited to, unsubstituted phenyl group, phenyl group having an alkyl group with a carbon number of 1 to 5 such as 4-methylphenyl group, 3,5-dimethylphenyl group, etc., phenyl group having a halogen substituent such as 4-fluorophenyl group, 4-chlorophenyl group, etc., and phenyl group having an alkoxy group such as 4-methoxyphenyl group, etc.

Examples of the naphthyl group that may have a substituent include, but are not limited to, 1-naphthyl group, 2-naphthyl group, 1-naphthyl group and 2-naphthyl group having 1 to 7 methyl groups. Examples of the cycloalkyl group that may have a substituent include, but are not limited to, cycloalkyl group with a carbon number of 3 to 8, and cycloalkyl group having a lower alkyl group with a carbon number of 1 to 5 such as a methyl group, ethyl group, propyl group or t-butyl group, or having a halogen atom such as fluorine, chlorine, bromine, and iodine, etc.

Examples of the unsubstituted or substituted alicyclic group wherein the ring is formed by binding $R^1$ and $R^2$ include, but are not limited to, unsubstituted cycloalkane with a carbon number of 4 to 7 wherein the ring is formed by binding $R^1$ and $R^2$, such as cyclobutane ring, cyclopentane ring, cyclohexane ring or cycloheptane ring, etc. or cycloalkane with a carbon number of 4 to 7 having a substituent such as a lower alkyl group with a carbon number of 1 to 5, e.g. a methyl group, ethyl group, propyl group and t-butyl group, etc., or a substituent such as a halogen atom, e.g. fluorine, chlorine, bromine, and iodine, etc.

Among them, from the viewpoint of easiness of synthesis and commercial availability, $R^1$ and $R^2$ are preferably phenyl group or substituted phenyl group, particularly preferably phenyl group or phenyl group that is mono-, di-, tri-, tetra- or penta-substituted by a lower alkyl group with a carbon number of 1 to 5 such as a methyl group, ethyl group, propyl group or t-butyl group; or preferably $R^1$ and $R^2$ are bound to form a cyclopentane ring or cyclohexane ring.

In general formula (1), $R^3$ is one selected from the group consisting of alkyl group that may have a substituent, perfluoroalkyl group, phenyl group that may have a substituent, naphthyl group that may have a substituent, cycloalkyl group that may have a substituent, benzyl group that may have a substituent, piperidinyl group that may have a substituent, pyrrolidinyl group that may have a substituent, and camphor group that may have a substituent.

Examples of the alkyl group that may have a substituent include, but are not limited to, linear or branched alkyl group with a carbon number of 1 to 10 such as methyl group, ethyl group, n-propyl group, isopropyl group, n-butyl group, sec-butyl group, isobutyl group, tert-butyl group, isohexyl group, etc., or the above linear or branched alkyl group having a halogen atom such as fluorine, chlorine, bromine, iodine, etc., a nitrogen atom, a sulfur atom, etc.; for example, examples of the alkyl group having one or more fluorine atoms include fluoromethyl group, difluoromethyl group, etc., or perfluoroalkyl group such as trifluoromethyl group, pentafluoroethyl group, etc.

Examples of the phenyl group that may have a substituent include, but are not limited to, unsubstituted phenyl group, phenyl group having an alkyl group with a carbon number of 1 to 5 such as 4-methylphenyl group, 4-tert-butylphenyl group, 4-isopropylphenyl group, 3,5-dimethylphenyl group, 2,4,6-trimethylphenyl group, 2,4,6-triisopropylphenyl group, or phenyl group having a halogen substituent such as 4-fluorophenyl group, 3-chlorophenyl group, 4-chlorophenyl group, 2,3-dichlorophenyl group, 3,4-dichlorophenyl group, 2,4,6-trichlorophenyl group, etc., phenyl group having a nitro group such as 4-nitrophenyl group, and phenyl group having an alkoxy group such as 4-methoxyphenyl group, etc.

Examples of the naphthyl group that may have a substituent include, but are not limited to, 1-naphthyl group, 2-naphthyl group, 1-naphthyl group and 2-naphthyl group having 1 to 7 methyl groups. Examples of the cycloalkyl group that may have a substituent include, but are not limited to, cycloalkyl group with a carbon number of 3 to 8, such as cyclopropyl, cyclobutyl, cyclopentyl, cyclohexyl, cycloheptyl, cyclooctyl, etc.

Examples of the benzyl group that may have a substituent include, but are not limited to, unsubstituted benzyl group, benzyl group with a carbon number of 1 to 5 such as 2,6-dimethylbenzyl group, etc.

Examples of the piperidinyl group or pyrrolidinyl group that may have a substituent include, but are not limited to, unsubstituted piperidinyl group, and piperidinyl group having a substituent such as a lower alkyl group with a carbon number of 1 to 5, e.g. a methyl group, ethyl group, propyl group and t-butyl group, or a substituent such as a halogen atom, e.g. fluorine, chlorine, bromine and iodine, etc. Examples of the pyrrolidinyl group that may have a substituent include, but are not limited to, unsubstituted pyrrolidinyl group, and pyrrolidinyl group having a substituent such as a lower alkyl group with a carbon number of 1 to 5, e.g. a methyl group, ethyl group, propyl group and t-butyl group, or a substituent such as a halogen atom, e.g. fluorine, chlorine, bromine and iodine, etc.

Examples of the camphor group that may have a substituent include, but are not limited to, unsubstituted camphor group, and camphor group having a substituent such as an alkyl group with a carbon number of 1 to 5, e.g. a methyl group, ethyl group, propyl group and t-butyl group, etc., or a substituent such as a halogen atom, e.g. fluorine, chlorine, bromine and iodine, etc.

In general formula (1), $R^4$ is a hydrogen atom or an alkyl group. Examples of the alkyl group include, but are not limited to, linear or branched alkyl group with a carbon number of 1 to 5 such as methyl group, ethyl group, etc. Of these, from the viewpoint of obtaining a high catalyst activity, methyl group or hydrogen atom is preferred, and hydrogen atom is particularly preferred.

In general formula (1), Ar is benzene that may have a substituent or a cyclopentadienyl group that may have a substituent, which binds to M via a $\pi$ bond. Examples of the benzene that may have a substituent include, but are not limited to, unsubstituted benzene, toluene, o-, m- and p-xylene, o-, m- and p-cymene, 1,2,3-, 1,2,4- and 1,3,5-trimethylbenzene, 1,2,4,5-tetramethylbenzene, 1,2,3,4-tetramethylphenyl group and pentamethylbenzene, and benzene having an alkyl group with a carbon number of 1 to 3 such as hexamethylbenzene, etc.

Examples of the cyclopentadienyl group that may have a substituent include, but are not limited to, unsubstituted cyclopentadienyl group, cyclopentadienyl group having an alkyl group with a carbon number of 1 to 3 such as methylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, and 1,2,3,4,5-pentamethylcyclopentadienyl group, etc.

Of these, from the viewpoint of achieving high asymmetric yield and easiness in obtaining a raw material, Ar is preferably p-cymene, 1,3,5-trimethylbenzene, 1,2,4,5-tetramethylbenzene, hexamethylbenzene, 1,2,3,4,5-pentamethylcyclopentadienyl; Ar is particularly preferably p-cymene, 1,3,5-trimethylbenzene, and 1,2,3,4,5-pentamethylcyclopentadienyl.

In general formula (1), X is an anionic group. In this specification, an anionic group contains a halogen atom. Examples of the anionic group include, but are not limited to, fluorine group, chlorine group, bromine group, iodine group, tetrafluoroborate group, tetrahydroborate group, tetrakis[3,5-bis(trifluoromethyl)phenyl]borate group, acetoxy group, benzoyloxy group, (2,6-dihydroxybenzoyl)oxy group, (2,5-dihydroxybenzoyl)oxy group, (3-aminobenzoyl)oxy group, (2,6-methoxybenzoyl)oxy group, (2,4,6-triisopropylbenzoyl)oxy group, 1-naphtalene carboxylate group, 2-naphtalene carboxylate group, trifluoroacetoxy group, trifluoromethanesulfoxy group, trifluoromethanesulfonimide group, etc. Of these, from the viewpoint of easiness in obtaining a raw material, X is preferably a chlorine group, bromine group, iodine group, and trifluoromethanesulfoxy group; it is furthermore preferably a chlorine group and trifluoromethanesulfoxy group.

In addition, in general formula (1), n denotes 0 or 1, and when n is 0, then X is absent.

In general formula (1), M is either ruthenium, rhodium or iridium.

The asymmetric catalyst of the present invention represented by general formula (1) has a structure wherein an ethylenediamine derivative or cyclohexanediamine derivative ($R^3SO_2NHCHR^1CHR^2NHR^4$), that is a bidentate ligand, coordinates to ruthenium, rhodium or iridium. Since the structure of the ligand that provides high reactivity and asymmetric yield differs depending on the structure of a substrate, optimal ethylenediamine derivative or cyclohexanediamine derivative corresponding to the structure of the substrate can be selected.

Examples of the above ethylenediamine derivative include, but are not limited to, TsDPEN (N-(p-toluenesulfonyl)-1,2-diphenylethylenediamine), MsDPEN (N-methanesulfonyl-1,2-diphenylethylenediamine), N-(benzylsulfonyl)-1,2-diphenylethylenediamine, N-(cyclohexanesulfonyl)-1,2-diphenylethylenediamine, N-(2,5-dimethylbenzylsulfonyl)-1,2-diphenylethylenediamine, N-(sec-butylsulfonyl)-1,2-diphenylethylenediamine, N-methyl-N'-(p-toluenesulfonyl)-1,2-diphenylethylenediamine, N-(p-methoxyphenylsulfonyl)-1,2-diphenylethylenediamine, N-(p-chlorophenylsulfonyl)-1,2-diphenylethylenediamine, N-(m-chlorophenylsulfonyl)-1,2-diphenylethylenediamine, N-(2,3-dichlorophenylsulfonyl)-1,2-diphenylethylenediamine, N-(3,4-dichlorophenylsulfonyl)-1,2-diphenylethylenediamine, N-(2,4,6-trichlorophenylsulfonyl)-1,2-diphenylethylenediamine, N-trifluoromethanesulfonyl-1,2-diphenylethylenediamine, N-(2,4,6-trimethylbenzenesulfonyl)-1,2-diphenylethylenediamine, N-(2,4,6-triisopropylbenzenesulfonyl)-1,2-diphenylethylenediamine, N-(4-tert-butylbenzenesulfonyl)-1,2-diphenylethylenediamine, N-(2-naphthylsulfonyl)-1,2-diphenylethylenediamine, N-(1-naphthylsulfonyl)-1,2-diphenylethylenediamine, N-(4-nitrobenzenesulfonyl)-1,2-diphenylethylenediamine, N-(3,5-dimethylbenzenesulfonyl)-1,2-diphenylethylenediamine, N-pentamethylbenzenesulfonyl-1,2-diphenylethylenediamine, N-(10-camphorsulfonyl)-1,2-diphenylethylenediamine, etc.

Examples of the above cyclohexanediamine derivative include, but are not limited to, TsCYDN (N-(p-toluenesulfonyl)-1,2-cyclohexanediamine), MsCYDN (N-methanesulfonyl-1,2-cyclohexanediamine), N-(benzylsulfonyl)-1,2-cyclohexanediamine, N-(cyclohexanesulfonyl)-1,2-cyclohexanediamine, N-(2,5-dimethylbenzylsulfonyl)-1,2-cyclohexanediamine, N-(sec-butylsulfonyl)-1,2-cyclohexanediamine, N-methyl-N'-(p-toluenesulfonyl)-1,2-cyclohexanediamine, N-(p-methoxyphenylsulfonyl)-1,2-cyclohexanediamine, N-(p-chlorophenylsulfonyl)-1,2-cyclohexanediamine, N-(m-chlorophenylsulfonyl)-1,2-cyclohexanediamine, N-(2,3-dichlorophenylsulfonyl)-1,2-cyclohexanediamine, N-(3,4-dichlorophenylsulfonyl)-1,2-cyclohexanediamine, N-(2,4,6-trichlorophenylsulfonyl)-1,2-cyclohexanediamine, N-trifluoromethanesulfonyl-1,2-cyclohexanediamine, N-(2,4,6-trimethylbenzenesulfonyl)-1,2-cyclohexanediamine, N-(2,4,6-triisopropylbenzenesulfonyl)-1,2-cyclohexanediamine, N-(4-tert-butylbenzenesulfonyl)-1,2-cyclohexanediamine, N-(2-naphthylsulfonyl)-1,2-cyclohexanediamine, N-(1-naphthylsulfonyl)-1,2-cyclohexanediamine, N-(4-nitrobenzenesulfonyl)-1,2-cyclohexanediamine, N-(3,5-dimethylbenzenesulfonyl)-1,2-cyclohexanediamine, N-pentamethylbenzenesulfonyl-1,2-cyclohexanediamine, N-(10-camphorsulfonyl)-1,2-cyclohexanediamine, etc.

Preparation methods of ruthenium, rhodium and iridium complexes represented by general formula (1) are described in Angew. Chem., Int. Ed. Engl. Vol. 36, p285 (1997), J. Org. Chem. Vol. 64, p 2186 (1999) and others. Namely, they can be synthesized by reacting a ruthenium, rhodium or iridium complex having a ligand X with a sulfonyldiamine ligand. Alternatively, they can be synthesized by reacting a metal amide complex having a sulfonyldiamine ligand with HX.

Examples of a ruthenium complex as a starting material of the ruthenium complex represented by general formula (1) include, for example, inorganic ruthenium compounds such as ruthenium (III) chloride hydrate, ruthenium (III) bromide hydrate, ruthenium (III) iodide hydrate, etc., ruthenium compounds with coordination of diene such as [ruthenium dichloride(norbornadiene)]polynuclear complex, [ruthenium dichloride(cycloocta-1,5-diene)]polynuclear complex bis(methylallyl)ruthenium(cycloocta-1,5-diene), etc., ruthenium complexes with coordination of an aromatic compound such as [ruthenium dichloride(benzene)]polynuclear complex, [ruthenium dichloride(p-cymene)]polynuclear complex, [ruthenium dichloride(trimethylbenzene)]polynuclear complex, [ruthenium dichloride(hexamethylbenzene)]polynuclear complex, etc., and complexes with coordination of phosphine such as dichlorotris(triphenylphosphine)ruthenium, etc., ruthenium dichloride(dimethylformamide)4, chlorohydridetris(triphenylphosphine)ruthenium, etc. In addition, examples are not particularly limited to the above compounds, as long as they are a ruthenium complex having a ligand that is replaceable with an optically active diphosphine compound or an optically active diamine compound. For example, various ruthenium complexes described in Comprehensive Organometallic Chemistry II Vol. 7 p 294-296 (Pergamon) can be used as a starting material.

Similarly, examples of rhodium and iridium complexes as a starting material of the asymmetric rhodium complex and asymmetric iridium complex represented by general formula (1) include, for example, inorganic rhodium compounds such as rhodium (III) chloride hydrate, rhodium (III) bromide hydrate, rhodium (III) iodide hydrate, etc., [pentamethylcyclopentadienyl rhodium dichloride]polynuclear complex, [pentamethylcyclopentadienyl rhodium dibromide]polynuclear complex, and [pentamethylcyclopentadienyl rhodium diiodide]polynuclear complex.

Reaction of a ruthenium, rhodium or iridium complex as a starting material with a ligand is carried out in one or more solvents selected from the group consisting of aromatic hydrocarbon solvents such as toluene and xylene, aliphatic hydrocarbon solvents such as pentane and hexane, halogen-containing hydrocarbon solvents such as methylene chloride, ether solvents such as diethylether and tetrahydrofurane, alcohol solvents such as methanol, ethanol, 2-propanol, butanol and benzyl alcohol, and organic solvents containing heteroatoms, such as acetonitrile, DMF, N-methylpyrrolidone and DMSO, at a reaction temperature between 0° C. and 200° C.; a metal complex can be obtained from this reaction.

Furthermore, in some cases metal complex catalysts represented by general formula (1) contain one or more organic compounds that are the reaction reagent used in the synthesis. Here, the organic compounds refer to coordinated organic solvent, and their examples include aromatic hydrocarbon solvents such as toluene and xylene, aliphatic hydrocarbon solvents such as pentane and hexane, halogen-containing hydrocarbon solvents such as methylene chloride, ether solvents such as ether and tetrahydrofurane, alcohol solvents such as methanol, ethanol, 2-propanol, butanol and benzyl alcohol, ketone solvents such as acetone, methyl ethyl ketone and cyclohexyl ketone, and organic solvents containing heteroatoms such as acetonitrile, DMF, N-methylpyrrolidone, DMSO and triethylamine.

Any of the asymmetric carbons in the metal complex of the present invention represented by general formula (1) must be in all (R) forms or all (S) forms in order to obtain optically active alcohols. By selecting either (R) or (S) form, an optically active alcohol having a desired absolute configuration can be obtained with high selectivity. Here, when production of racemic alcohols or achiral alcohols is desired, these chiral carbons are not necessarily both (R) forms or both (S) forms; they can be independently in any forms.

The amount of a metal complex represented by general formula (1) used in the present invention can be employed at a S/C value of between 10 and 10,000, when the molar ratio of the ketone compound relative to the metal complex is expressed as S/C (S denotes substrate, C denotes catalyst); it is preferably between 100 and 5,000 from the viewpoint of reaction efficiency and economic efficiency, and more preferably between 100 and 2,000.

The aliphatic ketone having one or more fluorine atoms at α position of the present invention is represented by general formula (2):

[Chem. 4]

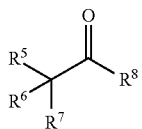

(2)

In general formula (2), $R^5$, $R^6$ and $R^7$ are an alkyl group with a carbon number of 1 to 5 which may contain hydrogen, fluorine atom or heteroatom (except that at least one of $R^5$, $R^6$ and $R^7$ is a fluorine atom), $R^8$ is an alkyl group with a carbon number of 1 to 5 which may contain a heteroatom.

Examples of $R^5$, $R^6$ and $R^7$, i.e., the alkyl group with a carbon number of 1 to 5 which may contain a heteroatom include, but are not limited to, linear or branched alkyl group with a carbon number of 1 to 5 such as methyl group, ethyl group, n-propyl group, isopropyl group, n-butyl group, sec-butyl group, tert-butyl group, etc., and the above linear or branched alkyl group with a carbon number of 1 to 5 having, as a heteroatom, a halogen atom such as fluorine, chlorine, bromine and iodine, etc., and an oxygen atom, a sulfur atom and a nitrogen atom. The carbon number is, from the viewpoint of isolation and purification by means of distillation of products, preferably 1 to 3, and more preferably 1 to 2.

Examples of $R^8$, i.e., the alkyl group with a carbon number of 1 to 5 which may contain a heteroatom include, but are not limited to, linear or branched alkyl group with a carbon number of 1 to 5 such as methyl group, ethyl group, n-propyl group, isopropyl group, n-butyl group, sec-butyl group, tert-butyl group, etc., and the above linear or branched alkyl group with a carbon number of 1 to 5 having, as a heteroatom, a halogen atom such as fluorine, chlorine, bromine and iodine, etc., and an oxygen atom, a sulfur atom and a nitrogen atom, preferably having a halogen atom except fluorine atom. The carbon number is, from the viewpoint of isolation and purification by means of distillation of products, preferably 1 to 3, and more preferably 1 to 2.

In one embodiment of the present invention, $R^5$, $R^6$ and $R^7$ are an alkyl group with a carbon number of 1 to 2 which may contain hydrogen, fluorine or a heteroatom (except that at least one of them is a fluorine atom), and $R^8$ is an alkyl group with a carbon number of 1 to 3 which may contain a heteroatom except fluorine atom.

In one embodiment of the present invention, $R^5$, $R^6$ and $R^7$ are hydrogen or fluorine (here, at least one of them is a fluorine atom), and $R^8$ is an alkyl group with a carbon number of 1 to 2.

Representative examples of the aliphatic ketone having a fluorine atom at α position represented by general formula (2) include: 1,1,1-trifluoroacetone, 1,1-difluoroacetone, 1-fluoroacetone, 1,1,1-trifluoro-2-butanone, 1,1-difluoro-2-butanone, 1-fluoro-2-butanone, 1,1,1-trifluoro-2-pentanone, 1,1-difluoro-2-pentanone, 1-fluoro-2-pentanone, 1,1,1-trifluoro-2-hexanone, 1,1-difluoro-2-hexanone, 1-fluoro-2-hexanone, 3,3,4,4,4-pentafluoro-2-butanone, 3,3,4,4-tetrafluoro-2-butanone, 3,3,4-trifluoro-2-butanone, 3,3-difluoro-2-butanone, 3,4,4,4-tetrafluoro-2-butanone, 3,4,4-trifluoro-2-butanone, 3,4-difluoro-2-butanone, 3-fluoro-2-butanone, 1,1,1,2,2-pentafluoro-3-pentanone, 1,1,2,2-tetrafluoro-3-pentanone, 1,2,2-trifluoro-3-pentanone, 2,2-difluoro-3-pentanone, 1,1,1,2-tetrafluoro-2-pentanone, 1,1,2-trifluoro-3-pentanone, 1,2-difluoro-3-pentanone, 2-fluoro-3-pentanone, 3,3,4,4,5,5,5-heptafluoro-2-pentanone, 3,3,4,4,5,5-hexafluoro-2-pentanone, 3,3,4,4,5-pentafluoro-2-pentanone, 3,3,4,4-tetrafluoro-2-pentanone, 3,3,4,5,5,5-hexafluoro-2-pentanone, 3,3,4,5,5-pentafluoro-2-pentanone, 3,3,4,5-tetrafluoro-2-pentanone, 3,3,4-trifluoro-2-pentanone, 3,3,5,5,5-pentafluoro-2-pentanone, 3,3,5,5-tetrafluoro-2-pentanone, 3,3,5-trifluoro-2-pentanone, 3,3-difluoro-2-pentanone, 3,4,4,5,5,5-hexafluoro-2-pentanone, 3,4,4,5,5-pentafluoro-2-pentanone, 3,4,4,5-hexafluoro-2-pentanone, 3,4,4-trifluoro-2-pentanone, 3,4,5,5,5-pentafluoro-2-pentanone, 3,4,5,5-tetrafluoro-2-pentanone, 3,4,5-trifluoro-2-pentanone, 3,4-difluoro-2-pentanone, 3,5,5,5-tetrafluoro-2-pentanone, 3,5,5-trifluoro-2-pentanone, 3,5-difluoro-2-pentanone, 3-fluoro-2-pentanone, etc.

A hydrogen source used in the present invention is preferably formate, from the viewpoint of easiness of separation from products. Examples of the formate include, but are not limited to, a salt of formic acid and alkaline metal or alkaline earth metal; specifically, lithium formate, sodium formate, potassium formate, cesium formate, magnesium formate, calcium formate, etc. From the viewpoint of obtaining high reactivity, it is preferably potassium formate or sodium formate, and potassium formate is more preferable. One or more of these may be combined.

Acid is necessary in the reaction, from the viewpoint of obtaining high alcohol yield and high optical purity; the kind of acid is not particularly limited, and examples of inorganic acid include hydrochloric acid, sulfuric acid, nitric acid, phosphoric acid, and perchloric acid; examples of organic acid include formic acid, acetic acid, oxalic acid, tartaric acid, citric acid, etc. One or more of these may be combined.

The amount of acid used is, from the viewpoint of asymmetric yield, in a molar equivalent range from 0.01 to 1 relative to the ketone substrate used, and preferably from 0.01 to 0.5, and more preferably from 0.01 to 0.2.

A solvent containing water used in the present invention is those which contain water as a main component; it may also contain other components such as alcohol, dimethyl sulfoxide, N,N-dimethylformamide, tetrahydrofurane, etc. Preferably, 90 mass % or more of the solvent is water, and more preferably 95 mass % or more of the solvent; and it is particularly preferably that the solvent consists of only water.

The present invention may be, in one embodiment, if necessary, carried out in the presence of phase-transfer catalyst. Examples of the phase-transfer catalyst include tetrabutylammonium fluoride, tetrabutylammonium chloride, tetrabutylammonium bromide, tetrabutylammonium iodide, tetrabutylammonium hydroxide, tetramethylammonium fluoride, tetramethylammonium chloride, tetramethylammonium bromide, tetramethylammonium iodide, tetramethylammonium hydroxide, benzyltrimethylammonium fluoride, benzyltrimethylammonium chloride, benzyltrimethylammonium bromide, benzyltrimethylammonium iodide, benzyltrimethylammonium hydroxide, tetraethylammonium fluoride, tetraethylammonium chloride, tetraethylammonium bromide, tetraethylammonium iodide, tetraethylammonium hydroxide, tetrapropylammonium fluoride, tetrapropylammonium chloride, tetrapropylammonium bromide, tetrapropylammonium iodide, tetrapropylammonium hydroxide, hexadecyltrimethylammonium fluoride, hexadecyltrimethylammonium chloride, hexadecyltrimethylammonium bromide, hexadecyltrimethylammonium iodide, hexadecyltrimethylammonium hydroxide, phenyltrimethylammonium fluoride, phenyltrimethylammonium chloride, phenyltrimethylammonium bromide, phenyltrimethylammonium iodide, phenyltrimethylammonium hydroxide, dodecyltrimethylammonium fluoride, dodecyltrimethylammonium chloride, dodecyltrimethylammonium bromide, dodecyltrimethylammonium iodide, dodecyltrimethylammonium hydroxide, benzyltriethylammonium fluoride, benzyltriethylammonium chloride, benzyltriethylammonium bromide, benzyltriethylammonium iodide, benzyltriethylammonium hydroxide, etc. In addition, one or more of these may be combined.

The amount of a phase-transfer catalyst added is in the range from 0.01 to 10 molar equivalents relative to the ketone substrate. Reactivity and enantioselectivity of the ketone substrate can be increased by the addition of a phase-transfer catalyst.

The value of reaction temperature is not particularly limited, but considering the boiling point of ketone substrates, it is in the range from 0° C. to 70° C., preferably from 20° C. to 60° C., and more preferably from 20° C. to 40° C.

Reaction time differs depending on the kind and concentration of reaction substrate, reaction conditions such as S/C and temperature, and the kind of catalyst; these conditions may be set such that the reaction is complete within several minutes to several days; in particular, it is preferably set such that the reaction is complete within 5 to 24 hours.

Purification of reaction products can be arbitrarily carried out by publicly-known methods such as column chromatography, distillation and recrystallization; however, distillation without extraction by a solvent is most preferred, because separation from the solvent becomes difficult and yield is decreased in extraction.

The asymmetric reduction of ketone substrates in the production process of the present invention can be performed either by a batch system or by a continuous system in terms of reaction system.

With the above method, optically active lower aliphatic fluoroalcohols with which separation from a solvent is difficult can be obtained efficiently with high purity. In the following, examples and comparative examples of the present invention are described and the present invention is explained in further detail; however, the invention should not be limited to these examples.

EXAMPLES

In the examples below, ketone substrates used were directly employed without purification of reagents purchased. With respect to reactors, a 100-mL glass autoclave was used with consideration given to volatilization of a substrate, unless otherwise stated. NMR was measured using JNM-LA400 (400 MHz, JEOL Ltd.). Regarding $^1$HNMR, tetramethylsilane (TMS) was used as the internal standard material, with its signal as δ=0 (δ refers to chemical shift). Conversion to alcohol compound and reaction yield were obtained by measurement using gas chromatography (GC), and by calculation using each value of integral of raw material, objective product and byproduct.

A conversion to alcohol compound is calculated by: [(sum of the integral values of objective product and byproduct)/(sum of the integral values of raw material, objective product and byproduct)]×100, and the reaction yield of alcohol compound is calculated by: [(number of moles of internal standard material added)×(integral value of objective product)/(integral value of internal standard material added)×(correction coefficient)/(number of moles of ketone body used)×100]. As for columns, DB-624 (30 m×0.53 mmϕ, DF=3.00 μm) (J&W Scientific Inc.) was used.

Optical purity was measured using GC, unless otherwise stated. As for columns, BGB-174 (30 m×0.25 mmϕ, DF=0.25 μm) (BGB Analytik AG) was used.

Comparative Example 1

Under argon gas atmosphere, a ruthenium complex RuCl[(S,S)-Tsdpen](mesitylene) (50 mg, 0.08 mmol), potassium formate (9.7 g, 115 mmol), tetrabutylammonium bromide (TBAB) (1.8 g, 5.6 mmol), water (11.2 mL) and 1,1,1-trifluoroacetone (5.0 mL, 56 mmol, substrate/catalyst ratio: 700) were introduced in a 100-mL glass autoclave. The container was sealed and stirred at room temperature for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 98.7%, and the yield of 1,1,1-trifluoro-2-propanol obtained with reference to the internal standard material was 75.8% relative to the amount of ketone used. Optical purity was 96.6% ee, and the absolute configuration was S form.

Comparative Examples 2-5

Reaction was carried out with the same conditions as comparative example 1, except that the reaction temperature, the amount of TBAB used, the amount of water used, and the reaction time were changed. Results are summarized in Table 1.

TABLE 1

$$F_3C-\overset{O}{\underset{}{\text{C}}}- \xrightarrow[\text{Potassium formate, TBAB, Water}]{\text{Metal complex}} F_3C-\overset{OH}{\underset{}{\text{C}}}-$$

| | Reaction temperature | Amount of TBAB (mol %/ketone) | Amount of water (mL) | Reaction time (h) | Conversion (%) | Alcohol yield (%) | Optical purity (% ee) |
|---|---|---|---|---|---|---|---|
| Comp. ex. 2 | Room temperature | Not used | 11.2 | 21 | 30.1 | Not measured | Not measured |
| Comp. ex. 3 | 60° C. | 5 | 5.6 | 4 | 100 | 33.8 | 93.9 |
| Comp. ex. 4 | 40° C. | 5 | 5.6 | 18 | 99.1 | 49.0 | Not measured |
| Comp. ex. 5 | 30° C. | 5 | 5.6 | 18 | 96.0 | 77.2 | 95.9 |

Example 1

Under argon gas atmosphere, a ruthenium complex RuCl[(S,S)-Tsdpen](mesitylene) (50 mg, 0.08 mmol), potassium formate (9.7 g, 115 mmol), tetrabutylammonium bromide (TBAB) (1.8 g, 5.6 mmol), water (5.6 mL), formic acid (0.63 mL, 16.7 mmol; 0.3 equivalent relative to the ketone used) and 1,1,1-trifluoroacetone (5.0 mL, 56 mmol, substrate/catalyst ratio: 700) were introduced in a 100-mL glass autoclave. The container was sealed and stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 99.3%, and the yield of 1,1,1-trifluoro-2-propanol obtained with reference to the internal standard material was 103% relative to the amount of ketone used. Optical purity was 94.6% ee, and the absolute configuration was S form.

Examples 2 to 8

Reaction was carried out with the same conditions as example 1, except that the reaction temperature, the amount of TBAB used, and the amount of formic acid used were changed. Results are summarized in Table 2.

From these results, the yield of the optically active 1,1,1-trifluoro-2-propanol was confirmed to be increased by the addition of an acid to the reaction system.

TABLE 2

$$F_3C\text{-CO-CH}_3 \xrightarrow[\text{Substrate/catalyst ratio} = 700]{\text{Metal complex, Potassium formate, TBAB, Water, formic acid}} F_3C\text{-CH(OH)-CH}_3$$

Reaction time 21 h

| | Reaction temperature | Amount of TBAB (mol %/ketone) | Amount of formic acid added (equivalent/ketone) | Conversion (%) | Alcohol yield (%) | Optical purity (% ee) | Alcohol yield/Conversion (%) |
|---|---|---|---|---|---|---|---|
| Ex. 2 | 40° C. | 5 | 0.3 | 100 | 100 | 94.9 | 100 |
| Ex. 3 | 30° C. | 5 | 0.2 | 100 | 99.1 | 95.4 | 99.1 |
| Ex. 4 | 30° C. | 5 | 0.1 | 100 | 101 | 96.3 | 101 |
| Ex. 5 | 30° C. | 5 | 0.4 | 69.5 | 66.2 | 94.2 | 95.2 |
| Ex. 6 | 30° C. | 5 | 0.5 | 78.9 | 79.0 | 93.6 | 100 |
| Ex. 7 | 30° C. | 5 | 0.05 | 100 | 99.9 | 96.4 | 99.9 |
| Ex. 8 | 30° C. | 2 | 0.1 | 100 | 104 | 95.6 | 104 |

Example 9

Under argon gas atmosphere, a ruthenium complex RuCl[(S,S)-Tsdpen](mesitylene) (50 mg, 0.08 mmol), potassium formate (9.7 g, 115 mmol), tetrabutylammonium bromide (TBAB) (0.36 g, 1.1 mmol), water (5.6 mL), formic acid (0.21 mL, 5.6 mmol; 0.1 equivalent relative to the ketone used) and 1,1,1-trifluoroacetone (5.0 mL, 56 mmol, substrate/catalyst ratio: 700) were introduced in a 100-mL three-necked flask equipped with a Dimroth condenser (cooling water of 0° C. is circulated). This was stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 100%, and the yield of 1,1,1-trifluoro-2-propanol obtained with reference to the internal standard material was 95.8% relative to the amount of ketone used. From these results, we confirmed that the objective substance can be obtained with high yield without using a pressure container.

Example 10

Under argon gas atmosphere, a ruthenium complex RuCl[(S,S)-BnSO$_2$dpen](mesitylene) (50 mg, 0.08 mmol), potassium formate (9.7 g, 115 mmol), tetrabutylammonium bromide (TBAB) (0.36 g, 1.1 mmol), water (5.6 mL), formic acid (0.21 mL, 5.6 mmol; 0.1 equivalent relative to the ketone used) and 1,1,1-trifluoroacetone (5.0 mL, 56 mmol, substrate/catalyst ratio: 700) were introduced in a 100-mL glass autoclave. The container was sealed and stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 100%, and the yield of 1,1,1-trifluoro-2-propanol obtained with reference to the internal standard material was 98.5% relative to the amount of ketone used. Optical purity was 94.4% ee, and the absolute configuration was S form.

Examples 11 to 30

For the optimization of metal complex, reaction was carried out with the same conditions as example 10, except that the metal complex was changed. Results are summarized in Table 3.

TABLE 3

$$F_3C\text{-CO-CH}_3 \xrightarrow[\text{Substrate/catalyst ratio} = 700]{\text{Metal complex, Potassium formate, TBAB, Water, formic acid}} F_3C\text{-CH(OH)-CH}_3$$

Reaction time 21 h

| | Metal Complex | Conversion (%) | Alcohol yield (%) | Optical purity (% ee) | Absolute configuration |
|---|---|---|---|---|---|
| Ex. 11 | Ru(OTf)I[(R)-Cs-(R,R)-dpen](mesitylene) | 67.9 | 60.6 | 92.2 | R |
| Ex. 12 | RuCl[(S,S)-4-tBuPhSO$_2$dpen](mesitylene) | 69.7 | 67.0 | 95.9 | S |
| Ex. 13 | RuCl[(S,S)-PhSO$_2$dpen](mesitylene) | 93.2 | 95.4 | 95.9 | S |
| Ex. 14 | RuCl[(S,S)-4-NO$_2$PhSO$_2$dpen](mesitylene) | 100 | 98.1 | 95.8 | S |
| Ex. 15 | RuCl[(S,S)-2,4-6-Me$_3$PhSO$_2$dpen](mesitylene) | 69.1 | 62.5 | 89.5 | S |
| Ex. 16 | RuCl[(R,R)-Msdpen](mesitylene) | 90.7 | 89.4 | 94.0 | R |
| Ex. 17 | RuCl[(R,R)-4-CF$_3$PhSO$_2$dpen](mesitylene) | 100 | 104 | 95.1 | R |
| Ex. 18 | RuCl[(S,S)-BiphenylSO$_2$dpen](mesitylene) | 65.1 | 56.6 | 95.4 | S |
| Ex. 19 | RuCl[(S,S)-2-NaphthylSO$_2$dpen](mesitylene) | 100 | 106 | 96.0 | S |

TABLE 3-continued $$F_3C-\overset{O}{\underset{\|}{C}}-CH_3 \xrightarrow[\substack{\text{Potassium formate, TBAB, Water,} \\ \text{formic acid} \\ \text{Substrate/catalyst ratio} = 700 \\ \text{Reaction time 21 h}}]{\text{Metal complex}} F_3C-\overset{OH}{\underset{|}{C}}H-CH_3$$

| Metal Complex | | Conversion (%) | Alcohol yield (%) | Optical purity (% ee) | Absolute configuration |
|---|---|---|---|---|---|
| Ex. 20 | RuCl[(S,S)-1-NaphthylSO$_2$dpen](mesitylene) | 100 | 94.7 | 95.4 | S |
| Ex. 21 | RuCl[(S,S)-4-iPrPhSO$_2$dpen](mesitylene) | 63.1 | 52.8 | 95.7 | S |
| Ex. 22 | RuCl[(R,R)-2,3-Cl$_2$PhSO$_2$dpen](mesitylene) | 100 | 108 | 95.8 | R |
| Ex. 23 | RuCl[(R,R)-2,4,6-Cl$_3$PhSO$_2$dpen](mesitylene) | 100 | 105 | 95.8 | R |
| Ex. 24 | RuCl[(R,R)-Tfdpen](mesitylene) | 44.0 | 34.4 | 85.6 | R |
| Ex. 25 | RuCl[(S,S)-4-iPrPhSO$_2$dpen](mesitylene) | 80.7 | 77.7 | 95.5 | S |
| Ex. 26 | Cp*Ir(OTf)[(S,S)-Msdpen] | 100 | 99.6 | 88.7 | S |
| Ex. 27 | Cp*RhCl[(S,S)-Msdpen] | 100 | 106 | 86.9 | S |
| Ex. 28 | RuCl[(R,R)-3-ClPhSO$_2$dpen](mesitylene) | 100 | 105 | 96.3 | R |
| Ex. 29 | RuCl[(R,R)-3,4-Cl$_2$PhSO$_2$dpen](mesitylene) | 100 | 98.6 | 96.3 | R |
| Ex. 30 | RuCl[(R,R)-3-MePhSO$_2$dpen](mesitylene) | 100 | 108 | 96.0 | R |

Example 31

Under argon gas atmosphere, a ruthenium complex RuCl[(S,S)-2-NaphthylSO$_2$dpen](mesitylene) (50 mg, 0.08 mmol), potassium formate (9.7 g, 115 mmol), tetrabutylammonium bromide (TBAB) (0.36 g, 1.1 mmol), water (5.6 mL), acetic acid (0.32 mL, 5.5 mmol; 0.1 equivalent relative to the ketone used) and 1,1,1-trifluoroacetone (5.0 mL, 56 mmol, substrate/catalyst ratio: 700) were introduced in a 100-mL glass autoclave. The container was sealed and stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material.

The conversion obtained from the amount of remaining ketone substrate was 100%, and the yield of 1,1,1-trifluoro-2-propanol obtained with reference to the internal standard material was 106% relative to the amount of ketone used. Optical purity was 96.4% ee, and the absolute configuration was S form.

Examples 32 to 34

In order to investigate effects of using other kinds of acid, reaction was carried out with the same conditions as example 31, except that RuCl[(S,S)-Tsdpen](mesitylene) was used as the ruthenium complex, and the kind and amount of acid added were changed. Results are summarized in Table 4.

These results confirmed that the similar effects could be obtained even when the kind of acid was changed.

TABLE 4

$$F_3C-\overset{O}{\underset{\|}{C}}-CH_3 \xrightarrow[\substack{\text{Potassium formate, TBAB, Water,} \\ \text{formic acid} \\ \text{Substrate/catalyst ratio} = 700 \\ \text{Reaction time 1 h,} \\ \text{Reaction temperature 30° C.}}]{\text{RuCl[(S,S)-Tsdpen](mestylene)}} F_3C-\overset{OH}{\underset{|}{C}}H-CH_3$$

| | Acid | Amount of acid added (mmol) | Conversion (%) | Alcohol yield (%) | Optical purity (% ee) |
|---|---|---|---|---|---|
| Ex. 32 | Hydrochloric acid | 5.5 | 100 | 109 | 96.2 |
| Ex. 33 | Sulfuric acid | 2.7 | 100 | 107 | 96.2 |
| Ex. 34 | Oxalic acid | 2.8 | 90.6 | 88.5 | 95.1 |

Example 35

Under argon gas atmosphere, a ruthenium complex RuCl[(S,S)-TSdpen](mesitylene) (0.51 g, 0.81 mmol), potassium formate (94.6 g, 1.12 mol), tetrabutylammonium bromide (TBAB) (9.00 g, 27.9 mmol), water (112 mL), formic acid (2.1 mL, 55.6 mmol; 0.1 equivalent relative to the ketone used) and 1,1,1-trifluoroacetone (50.0 mL, 559 mmol, substrate/catalyst ratio: 700) were introduced in a 300-mL SUS autoclave. The container was sealed and stirred at 30° C. for 21 h. After the reaction was complete, the reaction solution was distilled to obtain 61.2 g of (S)-1,1,1-trifluoro-2-propanol. The yield was 96%, and the purity measured by GC was 100%. Optical purity was 97.0% ee. Results of 1H-NMR measurement confirmed that these are objective products.

1H-NMR (CDCl3) 1.37 ppm (d, 3H), 3.0 ppm (br, 1H), 4.06-4.16 ppm (m, 1H)

Thus, it has been demonstrated that 1,1,1-trifluoro-2-propanol can be isolated with high yield by the present operation.

Example 36

Under argon gas atmosphere, a ruthenium complex RuCl[(S,S)-Tsdpen](mesitylene) (61.1 mg, 0.10 mmol), potassium formate (5.1 g, 60.9 mmol), tetrabutylammonium bromide (TBAB) (0.47 g, 1.5 mmol), water (6.0 mL), formic acid (0.11 mL, 2.9 mmol; 0.1 equivalent relative to the ketone used) and 1,1,1-trifluoro-2-butanone (4.0 mL, 29 mmol, substrate/catalyst ratio: 300) were introduced in a 100-mL glass autoclave. The container was sealed and stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 100%. Optical purity was 96.4% ee.

We confirmed that the reaction can proceed well with 1,1,1-trifluoro-2-butanone as well.

Example 37

Under argon gas atmosphere, a ruthenium complex RuCl[(S,S)-Tsdpen](mesitylene) (44.3 mg, 0.07 mmol), potassium formate (8.4 g, 99.3 mmol), tetrabutylammonium bromide (TBAB) (0.806 g, 2.50 mmol), water (5.6 mL), formic acid (0.20 mL, 5.3 mmol; 0.1 equivalent relative to the ketone used) and 1,1-difluoroacetone (4.0 mL, 50 mmol, substrate/catalyst ratio: 700) were introduced in a 100-mL glass autoclave. The container was sealed and stirred at 30° C. for 21 h. After the reaction was complete, the reaction solution was collected with dimethyl sulfoxide (DMSO), and GC was measured by adding N,N-dimethylformamide (1.0 mL, 12.9 mmol) as the internal standard material. The conversion obtained from the amount of remaining ketone substrate was 100%. Optical purity was obtained after conversion of the obtained alcohol into an MTPA ester, under the following conditions: (column: DB-5 (30 m×0.53 mm ID, film thickness 1.50 mm, J&W Scientific Inc.), temperature-increasing condition: 40° C.-3° C./min-250° C. (5 min), Pressure (He): 15.0 kPa, split ratio: 30), which was 82.7% ee.

We confirmed that the reaction can proceed well with 1,1-difluoroacetone as well.

INDUSTRIAL APPLICABILITY

The production process of optically active aliphatic alcohols of the present invention enables efficient synthesis of optically active lower aliphatic alcohols that have difficulty in separation from organic solvents, without using a special reactor.

The invention claimed is:

1. A process for producing an optically active fluoroalcohol, in which, under the presence of an acid and an asymmetric catalyst that is a metal complex represented by general formula (1):

[Chem. 1]

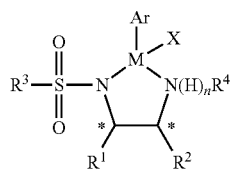

(1)

wherein $R^1$ and $R^2$ may be identical to or different from each other, and are one selected from the group consisting of an alkyl group that may have a substituent, a phenyl group that may have a substituent, a naphthyl group that may have a substituent, a cycloalkyl group that may have a substituent, and an unsubstituted or substituted alicyclic ring formed by binding $R^1$ and $R^2$, $R^3$ is one selected from the group consisting of an alkyl group that may have a substituent, a perfluoroalkyl group, a phenyl group that may have a substituent, a naphthyl group that may have a substituent, a cycloalkyl group that may have a substituent, a benzyl group that may have a substituent, a piperidinyl group that may have a substituent, a pyrrolidinyl group that may have a substituent, and a camphor group that may have a substituent, $R^4$ is a hydrogen atom or an alkyl group, Ar is benzene that may have a substituent or a cyclopentadienyl group that may have a substituent, which binds to M via a π bond, X is an anionic group, M is ruthenium, rhodium or iridium, n denotes either 0 or 1, and when n is 0, then X is absent, and

* denotes an asymmetric carbon;

an aliphatic ketone having one or more fluorine atoms at α position is reacted to produce an optically active alcohol in a solvent containing water, using a formate as a hydrogen source.

2. The production process according to claim 1, wherein the solvent containing water consists of only water.

3. The production process according to claim 1, wherein the formate is potassium formate and/or sodium formate.

4. The production process according to claim 1, wherein the acid is formic acid and/or acetic acid.

5. The production process according to claim 1, wherein the amount of addition of the acid is in the range from 0.01 to 1 molar equivalent relative to the ketone.

6. The production process according to claim 1, characterized in that the reaction is carried out in the presence of phase-transfer catalyst.

7. The production process according to claim 1, characterized in that the aliphatic ketone having one or more fluorine atoms at α position is a compound represented by general formula (2):

[Chem. 2]

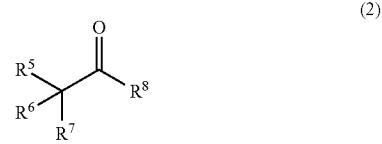

(2)

wherein $R^5$, $R^6$ and $R^7$ are hydrogen, fluorine, or an alkyl group with a carbon number of 1 to 5 which may contain a heteroatom (except that at least one of $R^5$, $R^6$ and $R^7$ is a fluorine atom), $R^8$ is an alkyl group with a carbon number of 1 to 6 which may contain a heteroatom.

8. The production process according to claim 7, wherein $R^5$, $R^6$ and $R^7$ are hydrogen, fluorine, or an alkyl group with a carbon number of 1 to 2 which may contain a heteroatom (except that at least one of $R^5$, $R^6$ and $R^7$ is a fluorine atom), $R^8$ is an alkyl group with a carbon number of 1 to 3 which may contain a heteroatom excluding a fluorine atom.

9. The production process according to claim 7, wherein $R^5$, $R^6$ and $R^7$ are hydrogen or fluorine (except that at least one of them is a fluorine atom), $R^8$ is an alkyl group with a carbon number of 1 to 2.

10. The production process according to claim 1, wherein the aliphatic ketone having one or more fluorine atoms at α position is 1,1,1-trifluoroacetone.

11. The production process according to claim 1, characterized in that after the reaction is complete, an optically active fluoroalcohol is obtained by distillation of the objective substance from the reaction solution without extraction with a solvent.

* * * * *